(12) United States Patent
Du et al.

(10) Patent No.: US 8,575,215 B2
(45) Date of Patent: Nov. 5, 2013

(54) TREATMENT OF NEURODEGENERATIVE AND CARDIOVASCULAR DISORDERS

(75) Inventors: Yangsheng Du, Westfield, IN (US); Martin R. Farlow, Indianapolis, IN (US); Ruyu Du, Carmel, IN (US)

(73) Assignee: Yansheng Du, Carmel, IN (US)

( * ) Notice: Subject to any disclaimer, the term of this patent is extended or adjusted under 35 U.S.C. 154(b) by 591 days.

(21) Appl. No.: 12/708,401

(22) Filed: Feb. 18, 2010

(65) Prior Publication Data

US 2010/0160433 A1 Jun. 24, 2010

Related U.S. Application Data

(63) Continuation of application No. 10/316,145, filed on Dec. 10, 2002, now abandoned.

(60) Provisional application No. 60/339,215, filed on Dec. 10, 2001.

(51) Int. Cl.
*A61K 31/235* (2006.01)

(52) U.S. Cl.
USPC .......................................... 514/544; 514/543

(58) Field of Classification Search
USPC ................................................ 514/543, 544
See application file for complete search history.

(56) References Cited

U.S. PATENT DOCUMENTS

| | | | |
|---|---|---|---|
| 4,959,503 | A | 9/1990 | Connor et al. |
| 5,981,583 | A | 11/1999 | Aggarwal et al. |
| 6,271,199 | B2 | 8/2001 | Brand et al. |
| 6,703,421 | B1 | 3/2004 | Nunokawa et al. |

FOREIGN PATENT DOCUMENTS

| | | |
|---|---|---|
| EP | 0 404 039 | 12/1990 |
| EP | 0 527 458 | 8/1992 |
| JP | 62-294634 | 12/1987 |
| JP | 02-152950 | 6/1990 |
| JP | 2001-523085 | 11/2001 |
| WO | WO 97/23202 | 7/1997 |
| WO | WO 98/25626 | 6/1998 |
| WO | WO 99/37616 | 7/1999 |
| WO | WO 99/65449 | 12/1999 |

OTHER PUBLICATIONS

Panet et al., "Activation of Nuclear Transcription Factor kappa B (NF-kB) is Essential for Dopamine-Induced Apoptosis in PC 12 Cellsm " J. Neurochem., 77:391-398 (2001).
Aubin et al., "Aspirin and Salicylate Protect Against MPTP-Induced Dopamine Depletion in Mice," J. Neurochem., 71(4):1635-1642 (1998).
Algeri et al., Caffeic Acid Phenethyl Ester Blocks Apoptosis Induced by Low Potassium in Cerebellar Granule Cells, Society for Neuroscience Abstracts 26, No. 1-2 (2000).
Baeuerle et al., "Function and Activation of NF kappaB in the Immune System," Annual Review of Immunology, 12:141-179 (1994).
The Merck Manual, 15$^{th}$ edition, pp. 515-519, 1380-1387, 2035-2036.
Calabrese et al., "NO Synthase and NO-Dependent Signal Pathways in Brain Aging and Neurodegenative Disorders: The Role of Oxidant /Antioxidant Balance,: Neurochem. Res. 25"1315-1341, 2000, Entrez-PubMed, PMID:11059804, abstract.
Chabrier et al., "Nitric Oxide Synthases: Targets for Therapeutic Strategies in Neurological Diseases," CMLS. Cell. Mol. Life Sci. 55:1029-1035 (1999).
Database ICAPLUS on STN, No. 1986:435142, Tseng et al., : "Effects of Some Phenolics on the Prostaglandin Synthesizing Enzyme System," Abstract, Chemical & Pharmaceutical Bulletin, 1986, 34(3), 1380-3.
Grunberger et al., "Preferential Cytotoxicity on Tumor Cells by Caffeic Acid Phenethyl Ester Isolated from Propolis," Experientia, 44:230-232 (1988).
Ilhan et al., "The Effects of Caffeic Acid Phenethyl Ester (CAPE) on Spinal Cord Ischemia/Reperfision Injury in Rabbits," European Journal of Cardio-Thoracic Surgery, 16:458-463 (1999).
Mandir et al., "Poly(ADP-ribose) Polymerase Activation Mediates 1-methyl-4-phenyl-1,2,3,6-tetrahydropyridine (MPTP)-induced Parkinsonism," Proc. Natl. Acad. Sci. USA 96:5774-5779 (1999).
Natarajan et al., "Caffeic Acid Phenethyl Ester is a Potent and Specific Inhibitor of Nuclear Transcription Factor NF-κB," Proc. Natl. Acad. Sci., USA 93:9090-9095 (1996).
Lin et al., "Minocycline Blocks Nitric Oxide-Induced Neurotoxicity by Inhibition p38 MAP Kinase in Rat Cerebellar Granule Neurons," Neurosci Lett Nov. 23, 2001:315(1-2):61-4, Entrez-PubMed, PMID:11711215, abstract.
Wermuth, Camille G., Part III, 1998 1$^{st}$ Edition, pp. 236-240.
Cooper et al., "L- Dopa esters as potential prodrugs: behavioural activity in experimental models of Parkinson's Disease,"J. Pharm. Pharmacol., 39:627-635 (1987).
Halliwell, Barry, "The Wanderings of a Free Radical," Free Radical Biology & Medicine, 46: 531-542 (2009).
LeWitt et al., "Protection Against Parkinson's Disease Progression: Clinical Experience," Neurotherapeutics: The Journal of the American Society for Experimental Neurotherapeutics, vol. 5, 210-215 (2008).

(Continued)

*Primary Examiner* — Shengjun Wang
(74) *Attorney, Agent, or Firm* — Cesari and McKenna, LLP

(57) ABSTRACT

A method of treating a neurodegenerative or cardiovascular disorder with a compound of the following formula:

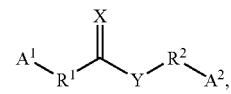

in which X, Y, $A^1$, $A^2$, $R^1$, and $R^2$ are defined herein.

7 Claims, No Drawings

(56) References Cited

OTHER PUBLICATIONS

The Parkinsons Group, "Effects of Tocopherol and Deprenyl on the Progression of Disability in Early Parkinson's Disease," The New England Journal of Medicine, 328: 176-183 (1993) [online: retrieved Mar. 1, 2010].

Shoulson et al., "Mortality in DATATOP: A Multicenter Trial in Early Parkinson's Disease," Annals of Neurology, vol. 43, 318-325 (1998).

Koizumi et al., "Screening of Caspase-3 Inhibitors in the Presence of Zinc Ion and Discovery of Novel, Non-Peptide Inhibitors," Society for Neuroscience, vol. 27, 2051 (2001).

Shimoke et al., "Nerve Growth Factor Prevents 1-Methyl-4-Phenyl-1,2,3,6-Tetrahydropyridine—Induced Cell Death Via the Akt Pathway by Suppressing Caspase-3-Like Activity Using PC12 Cells: Relevance to Therapeutical Application for Parkinson's Disease," Journal of Neuroscience Research, vol. 63, 402-409 (2001).

Hishikawa et al., The Japanese Journal of Pharmacology, Mar. 1, 2001, 85 (supp. 1.1), S3-4.

Chu et al., "Apoptosis Inducing Factor Mediates Caspase-Independent 1-Methyl-4-Phenylpyridinium Toxicity in Dopaminergic Cells," Journal of Neurochemistry, vol. 94, 1685-1695 (2005).

Lotharius et al., "Distinct Mechanisms Underlie Neurotoxin-Mediated Cell Death in Cultured Dopaminergic Neurons," Journal of Neuroscience, vol. 19, 1284-1293 (1999).

TREATMENT OF NEURODEGENERATIVE AND CARDIOVASCULAR DISORDERS

CROSS REFERENCE TO RELATED APPLICATION

This application is a continuation of U.S. application Ser. No. 10/316,145, filed on Dec. 10, 2002, which claims the benefit of U.S. provisional application 60/339,215, filed Dec. 10, 2001. The content of this applications is hereby incorporated by reference in its entirety.

BACKGROUND OF THE INVENTION

Nitric oxide (NO)-induced and caspase 1-related neuronal loss may lead to neurodegenerative disorders associated with neonatal and adult stroke, Parkinson's disease, Huntington's disease, Alzheimer's disease, amyothrophic lateral sclerosis, stroke, spinal injury, transplantation, multiple sclerosis, as well as hearing loss. No neuroprotective drug is available to these diseases. Some drugs are available for treating these diseases by enhancing the function of remaining neurons. However, no drug is very successful in slowing the progression of these disorders. Some of them even produce undesirable side effects, such as motor fluctuations and dyskinesias in Parkinson's disease. See, e.g., Quinn, et al., Neurology, 1998, 51, S25-29. Additionally, NO-induced and caspase 1-related heart cell loss may contribute to cardiovascular disorders, including heart failure, arteriosclerosis, myocarditis, and cardiomyopathy.

SUMMARY OF THE INVENTION

The present invention relates to a method of treating neurodegenerative and cardiovascular disorders and other disorders associated with NO-induced or caspase 1-related cell death. The method includes administering to the subject in need thereof one or more compounds of Formula (I):

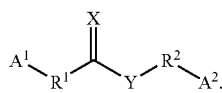
(I)

Each of $R^1$ and $R^2$, independently, is $C_{1-8}$ alkylene, $C_{2-8}$ alkenylene, or deleted; each of $A^1$ and $A^2$, independently, is aryl or heteroaryl, optionally mono- or multi- (e.g., di- or tri-) substituted with halogen, —CN, —NO$_2$, —OH, —SH, —OR$^3$, —SR$^3$, —R$^3$, —R$^3$—OR$^4$, —C(O)R$^3$, —S(O)R$^3$, —S(O)$_2$R$^3$, —NR$^4$R$^5$, —C(O)OR$^3$, —C(O)NR$^4$R$^5$, —O(O)CR$^4$, or —NR$^4$(O)CR$^5$, and each of X and Y, independently, is O, S, or NR$^6$, wherein each R$^3$ is $C_{1-4}$ alkyl, and each of R$^4$, R$^5$, and R$^6$, independently, is H or $C_{1-4}$ alkyl.

The term "alkyl" refers to a monovalent hydrocarbon radical, straight-chain or branched (e.g., —CH$_2$CH$_2$CH$_3$ or —CH(CH$_3$)$_2$). The term "alkylene" refers to a divalent hydrocarbon radical, straight-chain or branched (e.g., —CH$_2$CH$_2$— or —CH$_2$CH(CH$_3$)—CH$_3$). The term "alkenylene" refers to a divalent hydrocarbon radical, straight-chain or branched, containing one or more double bonds (e.g., —CH$_2$CH=CH—CH$_2$— or —CH$_2$CH(CH$_3$)CH=CH—CH$_2$—). The term "aryl" refers to a 6 to 12-carbon monocyclic or multicyclic (fused or separated) aromatic system wherein up to 4 atoms of each ring may be substituted. Examples of aryl groups include phenyl and naphthyl. The term "heteroaryl" refers to an aromatic 5-8 membered monocyclic, 8-12 membered bicyclic, or 11-14 membered tricyclic ring system, which contains 1-3 heteroatoms if monocyclic, 1-6 heteroatoms if bicyclic, or 1-9 heteroatoms if tricyclic (each heteroatom being O, N, or S). Examples of heteroaryl groups include pyridyl, furyl, imidazolyl, benzimidazolyl, pyrimidinyl, quinolinyl, indolyl, and thiazolyl.

Referring to Formula (I), each of X and Y, independently, is O in one subset of the compounds that can be used to practice the method of this invention. In another subset, $R^1$ is a $C_{2-8}$ alkenylene and $R^2$ is a $C_{1-8}$ alkylene. In still another subset, each of $A^1$ and $A^2$, independently, is aryl (e.g., phenyl), optionally substituted with halogen, —CN, —OH, —SH, —OR$^3$, —SR$^3$, —R$^3$, —R$^3$—OR$^4$, or —NR$^4$R$^5$. In still a further subset, $R^1$ is a $C_{2-3}$ alkenylene (e.g., —CH=CH—), and $R^2$ is a $C_{1-3}$ alkylene (e.g., —CH$_2$—CH$_2$—). One example of these compounds is caffeic acid phenethyl ester:

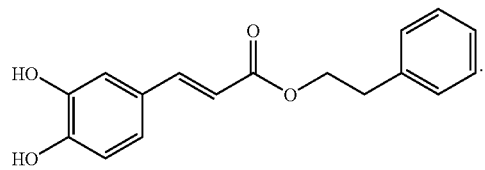

The neurodegenerative and cardiovascular disorders that can be treated by the method of this invention result from NO-induced or caspase 1-related cell loss, as well as from decrease in the amount of dopamine or the number of dopaminergic neurons. Such disorders are associated with a number of diseases, e.g., neonatal and adult stroke, Parkinson's disease, Huntington's disease, Alzheimer's disease, amyothrophic lateral sclerosis, stroke, spinal injury, transplantation, multiple sclerosis, hearing loss, heart failure, arteriosclerosis, myocarditis, cardiomyopathy, and diabetes. Thus, within the scope of this invention is use of one or more of the above-described compounds as a drug for treating these disorders.

One or more of the compound described above are formulated into a pharmaceutical composition before they are administered to a subject in need of treatment of a neurodegenerative or cadiovacular disorder. The invention therefore also relates to a pharmaceutical composition containing a pharmaceutically acceptable carrier and one or more of the compounds described above in an amount effective for treating a neurodegenerative or cardiovascular disorder. In another aspect, the invention further relates to an article of manufacture. The article includes: i) a container; ii) a pharmaceutical composition containing a pharmaceutically acceptable carrier and one or more of the above-described compounds in an effective amount; and iii) a label, disposed on the container and having instructions for administration of the pharmaceutical composition for treating a neurodegenerative or cadiovacular disorder. The instructions can provide directions for administration of the pharmaceutical composition to a subject, e.g., for epidural, intrathecal, parenteral, or local administration.

Also within the scope of this invention is use of one or more of the above-described compounds for the manufacture of a medicament for the treatment of the neurodegenerative and cardiovascular disorders mentioned above.

The compounds described above also include their salts and prodrugs, if applicable. Such salts, for example, can be formed between a positively charged substituent (e.g., amino) in a compound described and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) in a compound described above can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing compounds described above.

The details of an embodiment of the invention are set forth in the description below. Other features, objects, and advantages of the invention will be apparent from the description and the claims.

DETAILED DESCRIPTION OF THE INVENTION

This invention relates to a method of treating neurodegenerative and cardiovascular disorders as well as other disorders related to NO-induced or caspase 1-related cell death by using one or more compounds of the following formula:

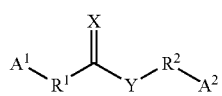

(I)

wherein each of $A^1$, $A^2$, $R^1$, $R^2$, and Y is defined above.

These compounds can be synthesized by methods well known in the art. For example, a compound in which X is O or S can be prepared by reacting a precursor of the formula $A^1$-$R^1$—C(=X)—OH with a precursor of the formula $A^2$-$R^2$—YH (Y is O, S, or NH). See, e.g., Loudon, Organic Chemistry, $3^{rd}$ Ed., 1995, Benjamin/Cummings Publishinh Company, Inc., Redwood, City, Calif. The compound thus obtained can be optionally converted to an imine (i.e., X is NH or N(alkyl)), e.g., via a reaction with ammonia or an amine. See, e.g., Verardo et al., Synth Commun, 1998, 18, 1501; and Farrar, Rec. Chem. Prog. 1968, 29, 85-101.

For instance, caffeic acid phenethyl ester can be synthesized by reacting caffeic acid with excess phenethyl alcohol in a suitable solvent (e.g., benzene) under reflux in the presence of an acid catalyst (e.g., p-toluene sulfonic acid) for an extended period of time (e.g., 3 or 4 days). Pure caffeic acid phenethyl ester (m.p. 126-128° C., needles) can be obtained after removal of excess phenethyl alcohol by distillation. See, e.g., Grunberger et al., Experientia, 1988, 44, 23-232.

A suitable compound of Formula (I) or its salt in an effective amount is formulated with a pharmaceutically acceptable carrier to form a pharmaceutical composition before it is administered to a subject in need of treatment of neurodegenerative and cardiovascular disorders as well as other disorders related to NO-induced or caspase 1-related cell death. "An effective amount" refers to the amount of the compound which is required to confer therapeutic effect on the treated subject, and can be determined based on animal and clinical studies. The interrelationship of dosages for animals and humans (based on milligrams per square meter of body surface) is described by Freireich et al., Cancer Chemother Rep, 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, and the optional co-usage with other therapeutic treatments. Examples of pharmaceutically acceptable carriers include colloidal silicon dioxide, magnesium stearate, cellulose, sodium lauryl sulfate, and D&C Yellow #10.

The pharmaceutical composition may be administered via a parenteral route, e.g., intraperitoneally and intravenously. Examples of parenteral dosage forms include an active compound dissolved in phosphate buffer saline (PBS), or admixed with any other pharmaceutically acceptable carrier. Solubilizing agents, such as cyclodextrins or other solubilizing agents well known to those familiar with the art, can also be included in the pharmaceutical composition.

One can assess the efficacy of a compound of Formula (I) on treating a neurodegenerative or cardiovascular disorder by both in vitro and in vivo assays well known in the art. See the three actual examples provided below.

Without further elaboration, it is believed that one skilled in the art can, based on the description herein, utilize the present invention to its fullest extent. All publications recited herein are hereby incorporated by reference in their entirety. The following specific examples, which describe biological testing of caffeic acid phenethyl ester, a compound of Formula (I), are, therefore, to be construed as merely illustrative, and not limitative of the remainder of the disclosure in any way whatsoever.

EXAMPLE 1

Efficacy of caffeic acid phenethyl ester on treating neurodegenerative disorders as well as other disorders related to NO-induced cell death was assessed by testing its ability to block NO-induced cell death on cultured neurons according to a method described in Du, et al., Proc Natl Acad Sci, 2001, 98, 14669-14674.

Significant neuron cell death in a cerebellar granule neurons (CGN) culture induced by nitric oxide was found to be blocked by caffeic acid phenethyl ester in a concentration-dependent manner ($IC_{50}$~1 µM). The neuroprotective effect of caffeic acid phenethyl ester was also observed when 6-hydroxydopamine was used to induce neurotoxicity.

EXAMPLE 2

Caffeic acid phenethyl ester was evaluated for its efficacy in treating a neurodegenerative disorder in mice. Three groups of eight-week-old male C57B1/6 mice (Taconic Farms Inc., Germantown, N.Y.), 5-7 per group, were used. A group of mice were administered for 9 days with caffeic acid phenethyl ester (5 or 20 mg/kg/day in 10% alcohol by oral gavage, or 40 mg/kg/day in 10% alcohol by intraperitoneal injection). As a control, a second group of mice were administered with 10% alcohol free of caffeic acid phenethyl ester. These two groups of mice then received four intraperitoneal injections of 1-methyl-4-phenyl-1,2,3,6-tetrahydropyridine ("MPTP")-HCl (20 mg/kg of free base) in saline at 2 hour intervals in a single day, as described in Liberatore, et al., Nat Med, 1999, 5, 1403-1409.

Seven days after the last administration of MPTP, the mice were anesthetized by halothane inhalation. Their brains were then removed and perfusion-fixed with 4% of paraformaldehyde in 0.1 M phosphate buffer (pH 7.4). After the fixation and subsequent cryoprotection in a 30% sucrose/phosphate buffer, the brains were frozen in liquid nitrogen and sectioned serially (40 µm) through the entire midbrain. The tissue sections were rinsed 3 times with 0.1 M PBS containing 0.1% Triton-X 100, 5 minutes each time. They were then incubated with rabbit polyclonal anti-tyrosine hydroxylase (anti-TH)

antibody (1:2,500, CALBIOCHEM, La Jolla, Calif.), goat biotinylated-conjugated polyclonal anti-rabbit antibody (1:250; Vector Laboratories, Burlingame, Calif.), horseradish-peroxidase conjugated avidin/biotin complex (VECTASTAIN ABC Reagent, Vector Laboratories), and successively exposed to diaminobenzidine for TH-immunohistochemistry analysis and stereological quantification of TH-positive neurons. The stereological method for counting TH-positive neurons is described in Triarhou, et al., J Neurocytol, 1988, 17, 221-232.

As another control, the third group of mice only received saline, i.e., free of both caffeic acid phenethyl ester and MPTP.

The number of TH-positive neurons in the substantia nigra pars compacta (SNpc) of the mice of the second group was approximately 49%, as compared with the mice of the third group. The mice in the first group showed a much higher number of TH-positive neurons (up to 100%) than the mice in the second group. Treatment of caffeic acid phenethyl ester alone for nine days did not significantly alter the number of TH-positive neurons.

The striatal levels of dopamine and its metabolites, dihydroxyphenylacetic acid (DOPAC) and homovanillic acid (HVA), were also determined by HPLC with electrochemical detector. See, e.g., Du, et al., Proc Natl Acad Sci, 2001, 98, 14669-14674. Comparison of data from the second group of mice and the third group of mice indicates that the striatal levels of dopamine, DOPAC, and HVA in the mice of the second group decreased by 62%, 46%, and 35%, respectively, 48 hours after the administration of MPTP without treatment with caffeic acid phenethyl ester. In the mice of the first group, caffeic acid phenethyl ester (40 mg/kg, intraperitoneally) significantly blocked the MPTP-induced decrease in the striatal levels of dopamine and its metabolites. More specifically, the caffeic acid phenethyl ester treatment resulted in MPTP-induced reduction of the striatal dopamine, DOPAC, and HVA levels by only 3%, −2%, and 16%, respectively.

These results indicate that caffeic acid phenethyl ester was unexpectedly effective in protecting neurons from death caused by MPTP.

EXAMPLE 3

An isolated working rabbit heart model was use to define the cardioprotective effects (function, metabolic and ultrastructure) of caffeic acid phenethyl ester during ischaemia by the method described in Choong, et al., J Cardiovasc Surg (Torino), 1993 October, 34(5):423-433. More specifically, hearts (n=7 for each group) were arrested with and exposed to reinfusion (45 min) throughout the ischaemic period with a cold (4° C.) cardioplegic solution. In an hour, caffeic acid phenethyl ester (30 mg/kg; intraperitoneal injection) significantly (p<0.05) improved the postischaemic recovery of cardiac output from 71.48+/−9.66% to 90.83+/−3.2%. The release of lactate dehydrogenase decreased during 40-minute ischaemic arrest (55.14+/−8.65 vs 19.33+/−7.4 IU/L perfusate for control and treatment, respectively; p<0.05). See Ersahin et al., J Cardiovasc Pharmacol, 1999 October; 34(4): 604-611. The results indicate that caffeic acid phenethyl ester protects myocardium against ischaemic injury and can thus be used to treat cardiac arrest.

Other Embodiments

Based on the above description, it will be understood that various modifications may be made without departing from the spirit and scope of the invention. Accordingly, other embodiments are within the scope of the following claims.

What is claimed is:

1. A method for treating Parkinson's disease, comprising administering to a subject in need thereof an effective amount of a compound of the following formula:

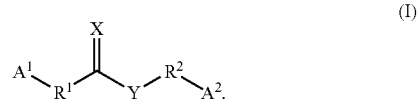

in which $R^1$ is —CH═CH—; $R^2$ is —CH$_2$—CH$_2$—; $A^1$ is 3,4-dihydroxyphenyl; $A^2$ is phenyl; and each of X and Y, independently, is O.

2. A method for treating Parkinson's disease, comprising administering to a subject in need thereof an effective amount of a compound of the following formula:

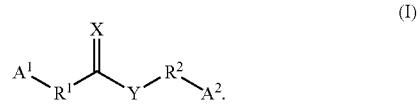

in which $R^1$ is —CH═CH—; $R^2$ is —CH$_2$—CH$_2$—CH$_2$—; $A^1$ is 3,4-dihydroxyphenyl; $A^2$ is phenyl; and each of X and Y, independently, is O.

3. A method for treating Parkinson's disease, comprising administering to a subject in need thereof an effective amount of a compound of the following formula:

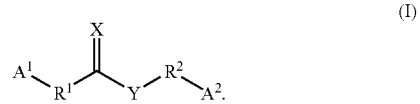

in which $R^1$ is —CH═CH—; $R^2$ is $C_{1-3}$ alkylene; $A^2$ is phenyl; $A^1$ is a 3,4-disubstituted phenyl, wherein the substituents are —OH or —O(O)CR$^4$, R$^4$ being $C_{1-4}$ alkyl, and each of X and Y, independently, is O.

4. The method of claim 3, wherein $R^2$ is —CH$_2$—CH$_2$— and $R^4$ is $C_{1-4}$ alkyl.

5. The method of claim 4, wherein $R^4$ is methyl.

6. The method of claim 3, wherein $R^2$ is —CH$_2$—CH$_2$—CH$_2$— and $R^4$ is $C_{1-4}$ alkyl.

7. The method of claim 6, wherein $R^4$ is methyl.

* * * * *